US012611197B2

(12) United States Patent
Okada et al.

(10) Patent No.: US 12,611,197 B2
(45) Date of Patent: Apr. 28, 2026

(54) ULTRASOUND DIAGNOSTIC APPARATUS AND CONTROL METHOD OF ULTRASOUND DIAGNOSTIC APPARATUS FOR DETECTING A SPECIFIC TARGET FROM AN ULTRASOUND IMAGE

(71) Applicant: FUJIFILM Corporation, Tokyo (JP)

(72) Inventors: Yuto Okada, Kanagawa (JP); Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 72 days.

(21) Appl. No.: 18/480,474

(22) Filed: Oct. 3, 2023

(65) Prior Publication Data

US 2024/0130716 A1    Apr. 25, 2024
US 2024/0225613 A9    Jul. 11, 2024

(30) Foreign Application Priority Data

Oct. 19, 2022    (JP) ................................. 2022-167844

(51) Int. Cl.
*A61B 8/00*       (2006.01)
*A61B 8/08*       (2006.01)

(52) U.S. Cl.
CPC .................. *A61B 8/54* (2013.01); *A61B 8/08* (2013.01); *A61B 8/463* (2013.01)

(58) Field of Classification Search
CPC ................................................... A61B 5/7264
See application file for complete search history.

(56) References Cited

U.S. PATENT DOCUMENTS

| | | | | |
|---|---|---|---|---|
| 2018/0140281 A1* | 5/2018 | Imai | ..................... | A61B 8/5207 |
| 2018/0160981 A1* | 6/2018 | Tsymbalenko | ....... | A61B 8/5215 |
| 2019/0005354 A1* | 1/2019 | Nakamura | ............. | G06N 20/00 |
| 2021/0121158 A1* | 4/2021 | Tsymbalenko | ....... | A61B 8/5246 |
| 2021/0128112 A1 | 5/2021 | Hatlan et al. | | |
| 2021/0287361 A1* | 9/2021 | Shriram | .................... | G06T 7/73 |
| 2021/0345993 A1 | 11/2021 | Dickie | | |

(Continued)

FOREIGN PATENT DOCUMENTS

JP          6419976 B2    11/2018

OTHER PUBLICATIONS

The extended European search report issued by the European Patent Office on Mar. 25, 2024, which corresponds to European Patent Application No. 23204491.7-1126 and is related to U.S. Appl. No. 18/480,474.

*Primary Examiner* — Nyrobi Celestine
(74) *Attorney, Agent, or Firm* — Studebaker Brackett PLLC

(57)          ABSTRACT
Provided are a control method of an ultrasound diagnostic apparatus and an ultrasound diagnostic apparatus capable of improving detection accuracy of a target inside a subject. An ultrasound diagnostic apparatus includes: an ultrasound probe; an image acquisition unit that acquires an ultrasound image of a subject using the ultrasound probe and in accordance with a plurality of parameters related to image acquisition; a specific target detection unit that detects a specific target from the ultrasound image using a machine learning model; and a preset setting unit that sets and supplies different presets to the image acquisition unit during an operation and during a non-operation of the specific target detection unit for a predetermined preset among the plurality of parameters.

7 Claims, 4 Drawing Sheets

(56)          References Cited

U.S. PATENT DOCUMENTS

2021/0353260 A1 * 11/2021 Srinivasa Naidu ..........................
                                   G01S 7/52098
2024/0099687 A1 * 3/2024 Roth ...................... G16H 40/63

* cited by examiner

ULTRASOUND DIAGNOSTIC APPARATUS AND CONTROL METHOD OF ULTRASOUND DIAGNOSTIC APPARATUS FOR DETECTING A SPECIFIC TARGET FROM AN ULTRASOUND IMAGE

CROSS-REFERENCE TO RELATED APPLICATIONS

The present application claims priority under 35 U.S.C. § 119 to Japanese Patent Application No. 2022-167844, filed on Oct. 19, 2022. The above application is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus for detecting a specific target from an ultrasound image.

2. Description of the Related Art

Conventionally, a subject has been examined by capturing an ultrasound image of an inside of the subject using a so-called ultrasound diagnostic apparatus. A user of the ultrasound diagnostic apparatus usually confirms the captured ultrasound image to determine whether or not a target such as an organ inside the subject is depicted in the ultrasound image. However, there may be cases where it may be difficult to accurately determine whether or not the target is depicted in the ultrasound image, depending on the image quality of the ultrasound image, the proficiency level of the user, and the like.

In that respect, a technology for automatically detecting a specific target inside a subject from an ultrasound image, for example, as disclosed in JP6419976B, has been developed. JP6419976B also discloses a technology for automatically setting imaging conditions of the ultrasound image, which include, for example, a so-called gain and the like, according to the detected target.

SUMMARY OF THE INVENTION

The target such as an organ inside the subject can be automatically detected by using the technology of JP6419976B, but there may be cases where detection accuracy decreases depending on the imaging conditions and types of the target in performing detection processing of the target.

The present invention has been made in order to solve such a conventional problem, and an object of the present invention is to provide an ultrasound diagnostic apparatus and a control method of an ultrasound diagnostic apparatus capable of improving detection accuracy of a target inside a subject.

According to the following configuration, the above-described object can be achieved.

[1] An ultrasound diagnostic apparatus comprising:
an ultrasound probe;
an image acquisition unit configured to acquire an ultrasound image of a subject using the ultrasound probe and in accordance with a plurality of parameters related to image acquisition;

a specific target detection unit configured to detect a specific target from the ultrasound image using a machine learning model; and
a preset setting unit configured to set and supply different presets to the image acquisition unit during an operation and during a non-operation of the specific target detection unit for a predetermined preset among the plurality of parameters.

[2] The ultrasound diagnostic apparatus according to [1], further comprising:
a monitor configured to display the ultrasound image; and
a display controller configured to display the ultrasound image on the monitor in different modes during the operation and during the non-operation of the specific target detection unit.

[3] The ultrasound diagnostic apparatus according to [2], in which the display controller is configured to display the preset, which is set by the preset setting unit and is different from the preset during the non-operation of the specific target detection unit, during the operation of the specific target detection unit on the monitor.

[4] The ultrasound diagnostic apparatus according to any one of [1] to [3], in which the preset setting unit is configured to set and supply the preset corresponding to the target, which is detected from the ultrasound image, to the image acquisition unit during the operation of the specific target detection unit.

[5] The ultrasound diagnostic apparatus according to any one of [1] to [4], in which the specific target detection unit is configured to detect, as the specific target, any of an organ, a blood vessel, a stool, a urine, a nerve, an ascites fluid, a pleural fluid, a suspected abnormal site, or a B-line.

[6] The ultrasound diagnostic apparatus according to any one of [1] to [5], in which the preset setting unit is configured to set at least one preset of a depth, a harmonic, a spatial compound, an acoustic power, a sound velocity, a steer, an ultrasound frequency, a gain, a dynamic range, or a contrast.

[7] A control method of an ultrasound diagnostic apparatus including an ultrasound probe, an image acquisition unit, a specific target detection unit, and a preset setting unit, the control method comprising:
causing the image acquisition unit to acquire an ultrasound image of a subject using the ultrasound probe and in accordance with a plurality of parameters related to image acquisition;
causing the specific target detection unit to detect a specific target from the ultrasound image using a machine learning model; and
causing the preset setting unit to set and supply different presets to the image acquisition unit during an operation and during a non-operation of the specific target detection unit for a predetermined preset among the plurality of parameters.

According to the present invention, an ultrasound diagnostic apparatus comprises: an ultrasound probe; an image acquisition unit that acquires an ultrasound image of a subject using the ultrasound probe and in accordance with a plurality of parameters related to image acquisition; a specific target detection unit that detects a specific target from the ultrasound image using a machine learning model; and a preset setting unit that sets and supplies different presets to the image acquisition unit during an operation and during a non-operation of the specific target detection unit for a predetermined preset among the plurality of parameters. Therefore, the detection accuracy of a target inside the subject can be improved.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment

Figure 1:
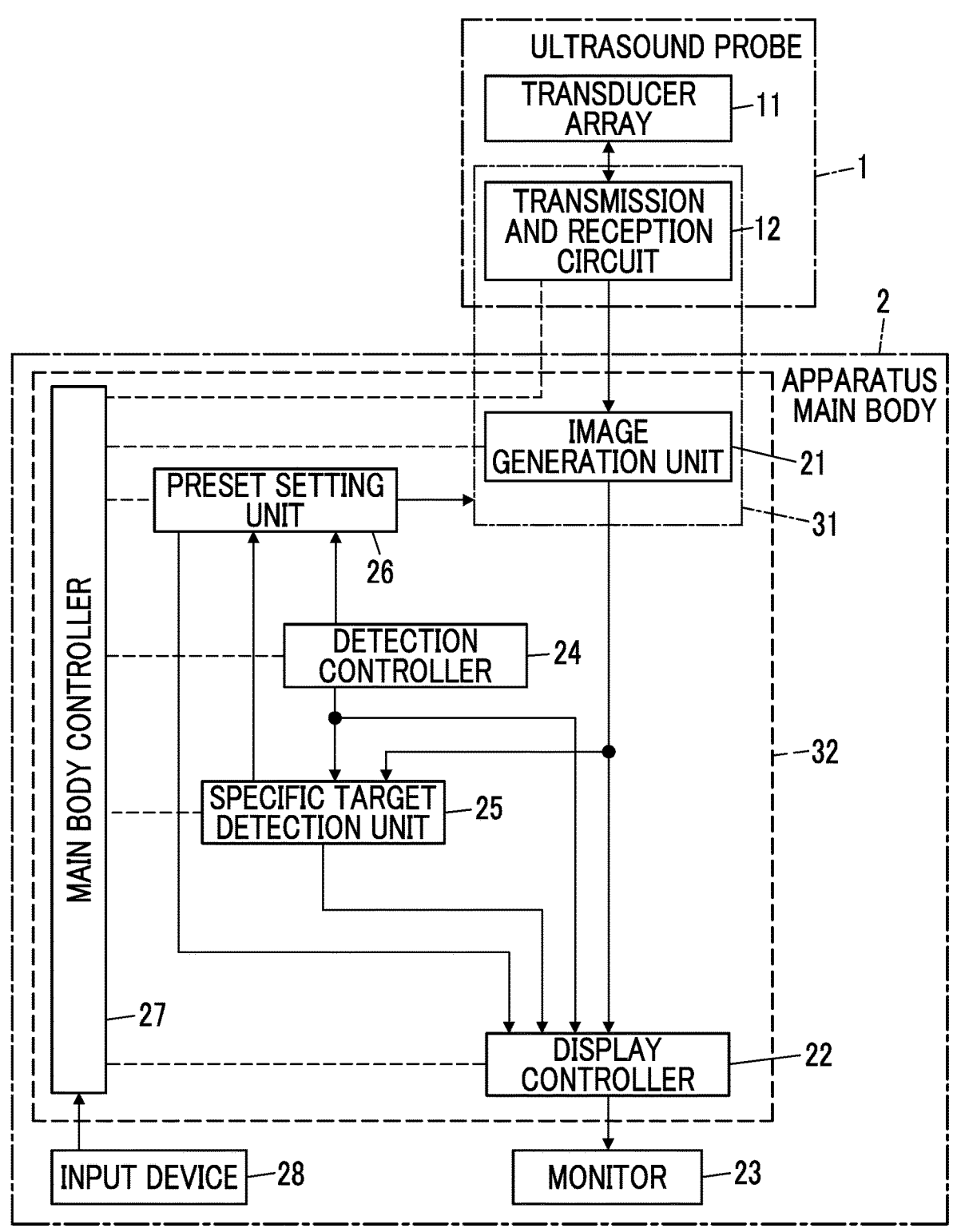
FIG. 1 is a block diagram showing a configuration of an ultrasound diagnostic apparatus according to an embodiment of the present invention.

FIG. 1 shows a configuration of an ultrasound diagnostic apparatus according to an embodiment of the present invention. The ultrasound diagnostic apparatus comprises an ultrasound probe 1 and an apparatus main body 2 connected to the ultrasound probe 1.

The ultrasound probe 1 includes a transducer array 11. A transmission and reception circuit 12 is connected to the transducer array 11.

The apparatus main body 2 includes an image generation unit 21 connected to the transmission and reception circuit 12 of the ultrasound probe 1. A display controller 22 and a monitor 23 are sequentially connected to the image generation unit 21. The transmission and reception circuit 12 and the image generation unit 21 constitute an image acquisition unit 31. In addition, the apparatus main body 2 comprises a detection controller 24. A specific target detection unit 25 is connected to the image generation unit 21 and the detection controller 24. A preset setting unit 26 is connected to the detection controller 24 and the specific target detection unit 25. The preset setting unit 26 is connected to the image acquisition unit 31. In addition, the detection controller 24, the specific target detection unit 25, and the preset setting unit 26 are connected to the display controller 22. Further, a main body controller 27 is connected to the image generation unit 21, the display controller 22, the detection controller 24, the specific target detection unit 25, and the preset setting unit 26. An input device 28 is connected to the main body controller 27.

Further, the image generation unit 21, the display controller 22, the detection controller 24, the specific target detection unit 25, the preset setting unit 26, and the main body controller 27 constitute a processor 32 for the apparatus main body 2.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission and reception circuit 12 and receives an ultrasound echo from a subject to output a signal based on the ultrasound echo. For example, each ultrasound transducer is composed of a piezoelectric body consisting of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like, and electrodes formed at both ends of the piezoelectric body.

Figure 2:
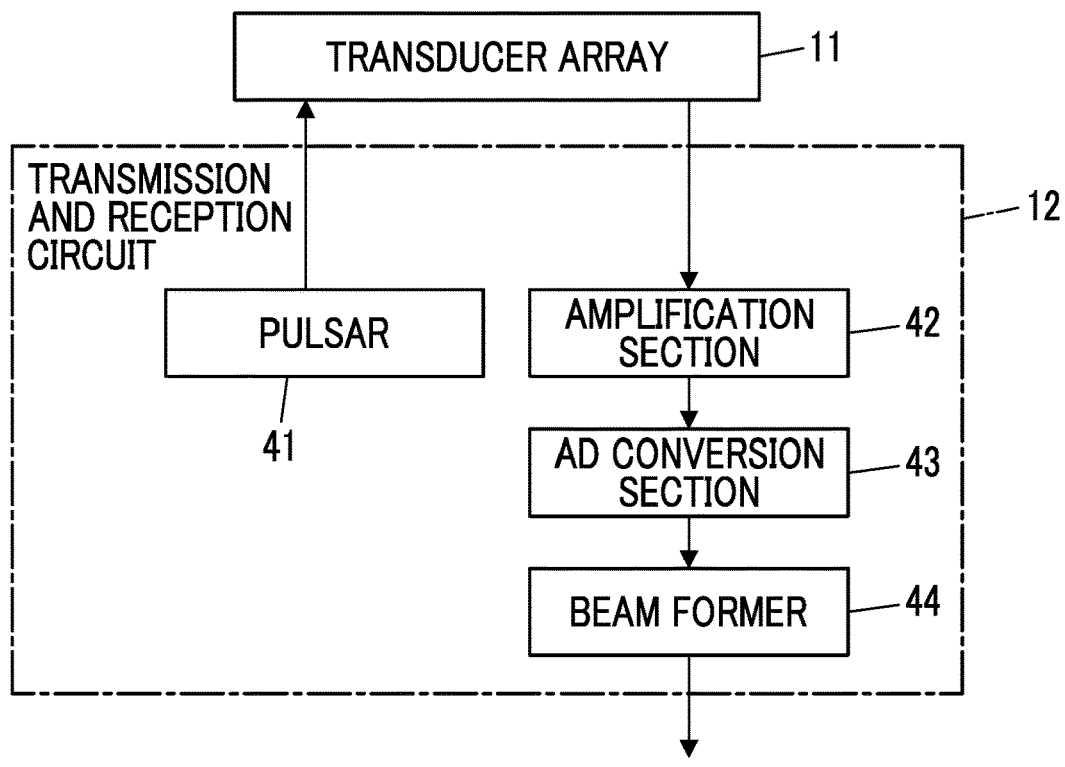
FIG. 2 is a block diagram showing a configuration of a transmission and reception circuit in the embodiment of the present invention.

The transmission and reception circuit 12 transmits the ultrasound wave from the transducer array 11 and generates a sound ray signal based on a reception signal acquired by the transducer array 11, under the control of the main body controller 27. As shown in FIG. 2, the transmission and reception circuit 12 includes a pulsar 41 connected to the transducer array 11, and an amplification section 42, an analog-to-digital (AD) conversion section 43, and a beam former 44 that are sequentially connected in series to the transducer array 11.

The pulsar 41 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 27. In this way, in a case where a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, whereby an ultrasound beam is formed from the combined wave of these ultrasound waves.

The transmitted ultrasound beam is reflected in, for example, a target such as a site of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
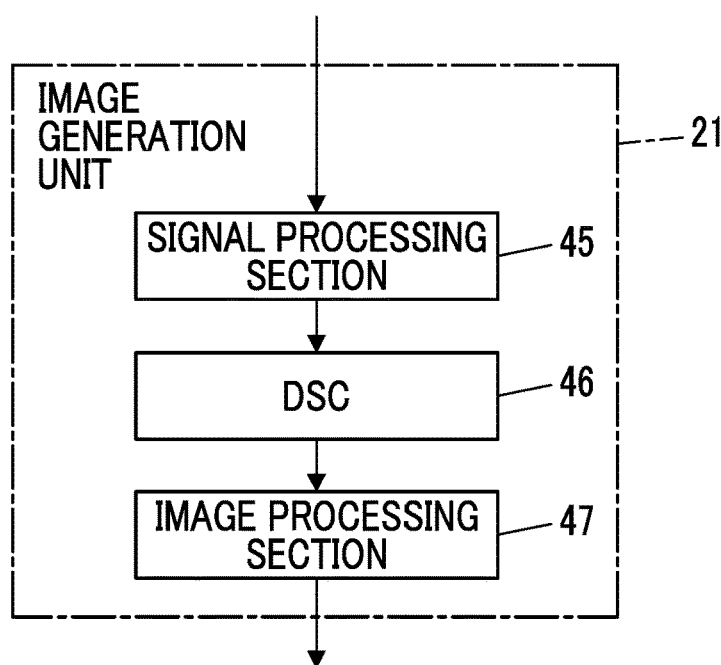
FIG. 3 is a block diagram showing a configuration of an image generation unit in the embodiment of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues inside the subject, by performing, on the sound ray signal received from the transmission and reception circuit 12, correction of the attenuation due to the distance according to the depth of the reflection position of the ultrasound wave using a sound velocity value set by the main body controller 27 and then performing envelope detection processing.

The DSC 46 converts (raster-converts) the B-mode image signal generated by the signal processing section 45 into an image signal in accordance with a normal television signal scanning method.

The image processing section 47 performs various types of necessary image processing such as gradation processing on the B-mode image signal input from the DSC 46 and then sends out the B-mode image signal to the display controller 22 and the specific target detection unit 25. Hereinafter, the B-mode image signal that has been subjected to image processing by the image processing section 47 is referred to as an ultrasound image.

The main body controller 27 controls each unit of the apparatus main body 2 and the ultrasound probe 1 in accordance with a program recorded in advance, or the like.

The input device 28 accepts an input operation from a user and sends out input information to the main body controller 27. The input device 28 is composed of, for example, a device that is used for the user to perform an input operation, such as a keyboard, a mouse, a trackball, a touchpad, or a touch panel.

The specific target detection unit 25 uses a so-called machine learning model to detect a specific target, for example, an organ, a blood vessel, a stool present inside the large intestine and a urine present inside the bladder, a nerve, an ascites fluid, a pleural fluid, a suspected abnormal site such as a tumor or a cyst, an artifact called a so-called B-line, and the like, from the ultrasound image generated by the image generation unit 21. The machine learning model has learned in advance a large number of ultrasound images showing the specific target inside the subject, and receives an input of the ultrasound image and then automatically analyzes the input ultrasound image to output a detection result of the specific target. In addition, the specific target detection unit 25 can also detect a size such as a length or a diameter of the specific target. For example, after detecting the target, the specific target detection unit 25 can measure the size of the detected target. In addition, the specific target detection unit 25 can also detect the size of the specific target from the ultrasound image including the target by using a machine learning model that has learned in advance a large number of combinations of a large number of ultrasound images showing the specific target inside the subject and size values measured for the target.

The detection controller 24 controls the specific target detection unit 25 to be in either an operation state or a non-operation state, based on, for example, an instruction from the user via the input device 28. In addition, the detection controller 24 designates the type of the target to be detected by the specific target detection unit 25 based on, for example, an instruction from the user via the input device 28. The specific target detection unit 25 performs processing of detecting a target designated by the detection controller 24 from the ultrasound image.

The preset setting unit 26 sets different presets during the operation and during the non-operation of the specific target detection unit 25 for a predetermined preset among a plurality of parameters related to the acquisition of the ultrasound image, such as a depth, the presence or absence of harmonic imaging, the presence or absence of a spatial compound, an acoustic power, a sound velocity, a steer angle, an ultrasound frequency, a gain, a dynamic range, or a contrast, and supplies the set preset to the image acquisition unit 31.

The preset refers to a value set in advance in at least one of the plurality of parameters related to the acquisition of the ultrasound image.

Usually, since the depth from the body surface, the size, the types of the surrounding tissue structures, the types of the surrounding organs, and the like differ for each target inside the subject, suitable values of the parameters for clearly depicting the target in the ultrasound image also differ. The preset setting unit 26 sets a preset such that the specific target designated by the detection controller 24 is particularly clearly depicted during the operation of the specific target detection unit 25, and supplies the set preset to the image acquisition unit 31. The image acquisition unit 31 can acquire an ultrasound image particularly clearly showing the specific target by using the supplied preset. The specific target detection unit 25 performs processing of detecting the specific target from the ultrasound image acquired in this manner, whereby the detection accuracy of the specific target can be improved.

In addition, the preset setting unit 26 can set a preset such that the entire ultrasound image is relatively clearly depicted during the non-operation of the specific target detection unit 25. The ultrasound image acquired in this manner is suitable for a case where the user confirms the entire ultrasound image, for example, in a case where the ultrasound image includes a plurality of organs.

As an example of the preset related to the depth, during the non-operation of the specific target detection unit 25, the preset can be set to 16 cm such that the plurality of organs can be easily confirmed, and in a case where the stool is designated as the specific target and during the operation of the specific target detection unit 25, the preset can be set to 12 cm such that the large intestine in which the stool is present can be confirmed larger.

As an example of the preset related to so-called sensitivity time control (STC), for example, during the non-operation of the specific target detection unit 25, the STC can be set to a value such that the plurality of organs can be easily confirmed, and in a case where the stool is designated as the specific target and during the operation of the specific target detection unit 25, the STC can be set to increase the gain at the depth where the large intestine is present and to reduce the gain at other depths in order to clearly depict the large intestine.

As an example of the preset related to the presence or absence of harmonic imaging, during the non-operation of the specific target detection unit 25, the preset can be set to acquire the ultrasound image using a so-called fundamental wave without using harmonic imaging, and in a case where the stool is designated as the specific target and during the operation of the specific target detection unit 25, the preset can be set to acquire the ultrasound image using harmonic imaging such that a difference between a so-called normal stool and a so-called hard stool is easily depicted.

As an example of the preset related to the presence or absence of the spatial compound, during the non-operation of the specific target detection unit 25, the preset can be set to acquire the ultrasound image without performing the spatial compound, and in a case where a blood vessel or the like present at a shallow position is designated as the specific target and during the operation of the specific target detection unit 25, the preset can be set to acquire the ultrasound image by performing the spatial compound such that the artifacts caused by multiple reflections near the body surface is suppressed and the target is clearly depicted.

As an example of the preset related to the acoustic power, during the non-operation of the specific target detection unit 25, the preset can be set to transmit ultrasound waves into the subject using a bipolar transmission waveform ranging from +50V to −50V in order to relatively clearly depict the entire ultrasound image, and in a case where the blood vessel or the like present in a shallow position is designated as the specific target and during the operation of the specific target detection unit 25, the preset can be set to transmit ultrasound waves into the subject using a bipolar transmission waveform with a relatively low acoustic power such as +25V to −25V in order to suppress the artifacts caused by multiple reflections near the body surface to clearly depict the target.

As an example of the preset related to the sound velocity, during the non-operation of the specific target detection unit 25, the preset can be set to 1540 m/s such that the entire ultrasound image is relatively clearly depicted, and in a case where a mammary gland or the like having a high amount of fat is designated as the specific target and during the operation of the specific target detection unit 25, the preset can be set to a relatively low sound velocity such as 1450 m/s such that the specific target is clearly depicted.

As an example of the preset related to the steer angle, during the non-operation of the specific target detection unit 25, the preset can be set to an angle of 0 degrees, that is, an angle approximately perpendicular to the body surface such that the entire ultrasound image is relatively clearly depicted, and in a case where the blood vessel or the like present at a shallow position is designated as the specific target for the purpose of inserting the puncture needle into the subject from the side of the ultrasound probe 1 and during the operation of the specific target detection unit 25, the preset can be set to an angle of 15 degrees or the like such that the target such as the puncture needle and the blood vessel is clearly depicted.

As an example of the preset related to the ultrasound frequency, during the non-operation of the specific target detection unit 25, a transmission frequency and a reception frequency of the ultrasound wave can be set to 7.5 MHz such that the entire ultrasound image is relatively clearly depicted, and in a case where the abdomen or the like having a fat is designated as the specific target and during the operation of the specific target detection unit 25, the transmission frequency and the reception frequency of the ultrasound wave can be set to 5 MHz such that the specific target is clearly depicted by increasing so-called penetration. As an example of the preset related to the gain, during the non-operation of the specific target detection unit 25, the preset can be set to 50 dB such that the entire ultrasound image is relatively clearly depicted, and in a case where the abdomen or the like having a fat is designated as the specific target and during the operation of the specific target detection unit 25, the preset can be set to 100 dB such that the specific target is clearly depicted by increasing the brightness of the entire ultrasound image.

As an example of the preset related to the dynamic range, during the non-operation of the specific target detection unit 25, the preset can be set to 65 dB such that the entire ultrasound image is relatively clearly depicted, and during the operation of the specific target detection unit 25, the preset can be set to 45 dB in order to increase the contrast to clearly depict the contour of the specific target.

The display controller 22 performs predetermined processing on the ultrasound image or the like generated by the image generation unit 21 and displays the ultrasound image or the like on the monitor 23, under the control of the main body controller 27.

In addition, the display controller 22 can display the ultrasound image on the monitor 23 in different modes during the operation and during the non-operation of the specific target detection unit 25. For example, the display controller 22 can display on the monitor 23 a specific target T without particular emphasis in the ultrasound image U as shown in FIG. 4 during the non-operation of the specific target detection unit 25, and can display on the monitor 23 the specific target T with emphasis, such as emphasizing a contour C of the target T in the ultrasound image U as shown in FIG. 5, during the operation of the specific target detection unit 25.

In addition, the display controller 22 can also display the preset, which is set by the preset setting unit 26 and is different from the preset during the non-operation of the specific target detection unit 25, on the monitor 23 during the operation of the specific target detection unit 25. In this case, the display controller 22 can display on the monitor 23, for example, as shown in FIG. 4, an icon A1 indicating a first preset set by the preset setting unit 26 during the non-operation of the specific target detection unit 25, and can display on the monitor 23, for example, as shown in FIG. 5, an icon A2 indicating a second preset different from the first preset during the operation of the specific target detection unit 25. In the example of FIG. 5, the icon A2 indicating that the STC is set to increase the gain at a specific depth is displayed on the monitor 23.

Figure 4:
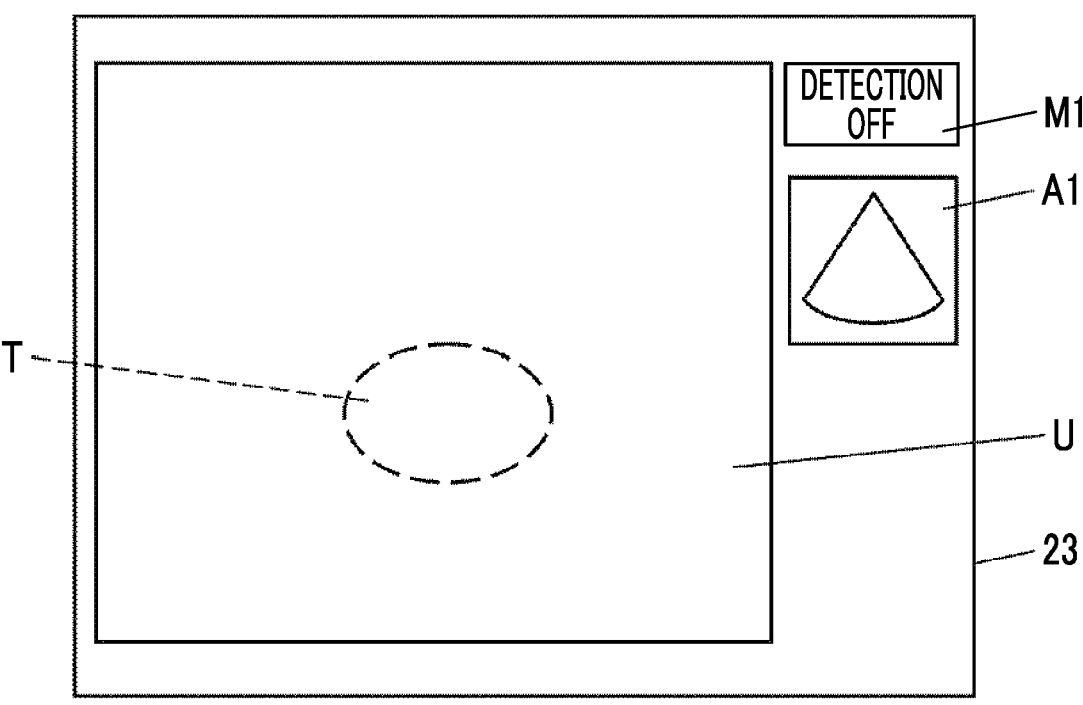
FIG. 4 is a diagram showing an example of a display screen of a monitor during a non-operation of the specific target detection unit.
Figure 5:
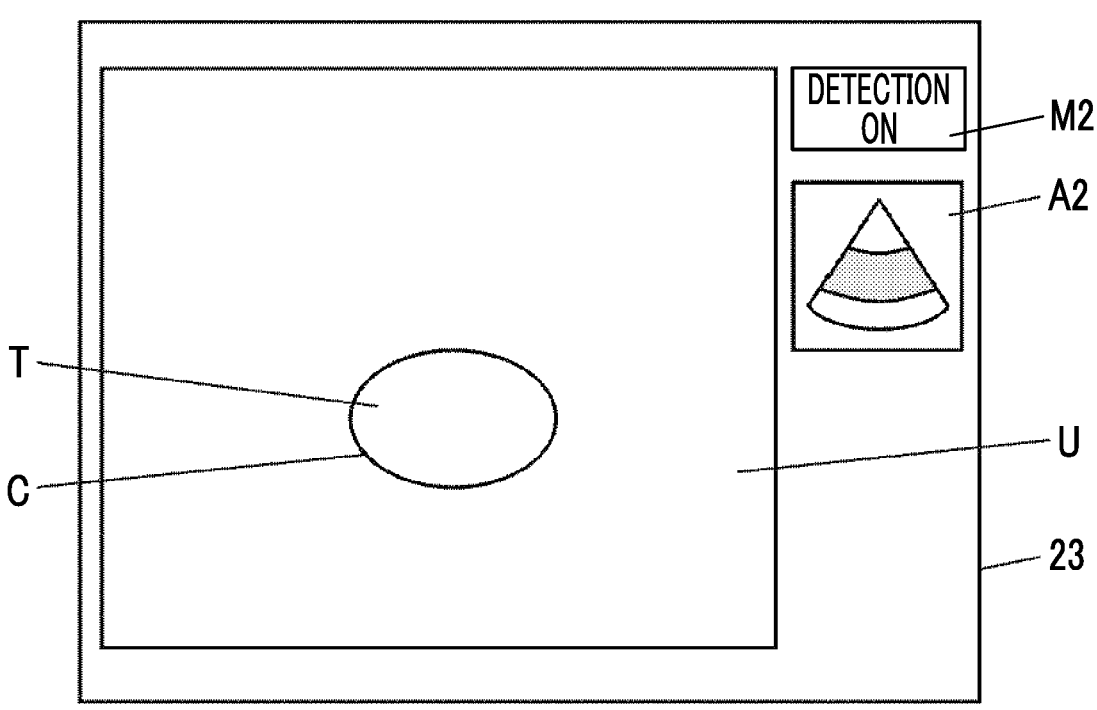
FIG. 5 is a diagram showing an example of a display screen of the monitor during an operation of the specific target detection unit.

Further, as shown in FIGS. 4 and 5, for example, the display controller 22 can also display on the monitor 23 a message M1 or a message M2 indicating whether or not the specific target detection unit 25 is operating.

The monitor 23 performs various kinds of display under the control of the display controller 22. The monitor 23 can include, for example, a display device such as a liquid crystal display (LCD) or an organic electroluminescence (EL) display.

Although the processor 32 including the image generation unit 21, the display controller 22, the detection controller 24, the specific target detection unit 25, the preset setting unit 26, and the main body controller 27 is composed of a central processing unit (CPU) and a control program for causing the CPU to perform various types of processing, the processor 32 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the detection controller 24, the specific target detection unit 25, the preset setting unit 26, and the main body controller 27 of the processor 32 can also be configured by being integrated partially or entirely into one CPU or the like.

Next, an example of the operation of the ultrasound diagnostic apparatus according to the embodiment will be described using the flowchart of FIG. 6.

First, in step S1, the detection controller 24 determines whether or not to execute the detection processing of the specific target T through the specific target detection unit 25. In this case, the detection controller 24 can determine to execute the detection processing of the specific target T, for example, in a case where an instruction to detect the target T is input from the user via the input device 28. In addition, the detection controller 24 can determine to not execute the detection processing of the specific target T, for example, in a case where no instruction to detect the target T is input from the user via the input device 28.

In a case where it is determined in step S1 to not execute the detection processing of the specific target T, the process proceeds to step S2. In step S2, the detection controller 24 controls the specific target detection unit 25 to be in the non-operation state, and the preset setting unit 26 sets the first preset for relatively clearly depicting the entire ultrasound image U and supplies the set first preset to the image acquisition unit 31.

In subsequent step S3, in a state in which the user disposes the ultrasound probe 1 on the body surface of the subject, the image acquisition unit 31 acquires the ultrasound image U using the first preset supplied in step S2. In this case, the transducer array 11 of the ultrasound probe 1 transmits the ultrasound beam into the subject and receives the ultrasound echo from the inside of the subject, thereby generating the reception signal. The transmission and reception circuit 12 of the image acquisition unit 31 performs so-called reception focus processing on the reception signal to generate the sound ray signal, under the control of the main body controller 27. The sound ray signal generated by the transmission and reception circuit 12 is sent out to the image generation unit 21. The image generation unit 21 generates the ultrasound image U using the sound ray signal sent out from the transmission and reception circuit 12.

In step S4, the display controller 22 displays the ultrasound image U on the monitor 23, for example, as shown in FIG. 4. In this case, the display controller 22 can display on the monitor 23 the message M1 indicating that the specific target detection unit 25 is in the non-operation state and the icon A1 indicating that the first preset is set. As a result, the user can easily grasp that the detection processing of the specific target T is not operating and the content of the first preset that is currently set.

In step S5, the detection controller 24 determines whether or not to execute the detection processing of the specific target T through the specific target detection unit 25. In this case, the detection controller 24 can determine to execute the detection processing of the specific target T, for example, in a case where an instruction to detect the target T is input from the user via the input device 28. In addition, the detection controller 24 can determine to not execute the detection processing of the specific target T, for example, in a case where no instruction to detect the target T is input from the user via the input device 28.

In a case where it is determined in step S5 to not execute the detection processing of the specific target T, the process proceeds to step S6. In step S6, the main body controller 27 determines whether or not to end the examination of the subject that is currently being performed. For example, the main body controller 27 can determine to end the examination in a case where an instruction to end the examination is input from the user via the input device 28, and can determine to continue the examination in a case where no instruction to end the examination is input from the user via the input device 28.

In a case where it is determined in step S6 to continue the examination, the process returns to step S3, and the ultrasound image U is newly acquired using the first preset. In subsequent step S4, the ultrasound image U is displayed on the monitor 23, and in step S5, it is determined whether or not to execute the detection processing of the specific target T. In a case where it is determined in step S5 to not execute the detection processing of the target T, the process proceeds to step S6. In this manner, as long as it is determined in step S5 to not execute the detection processing of the target T and it is determined in step S6 to continue the examination, the processing of steps S3 to S6 is repeated.

Figure 6:
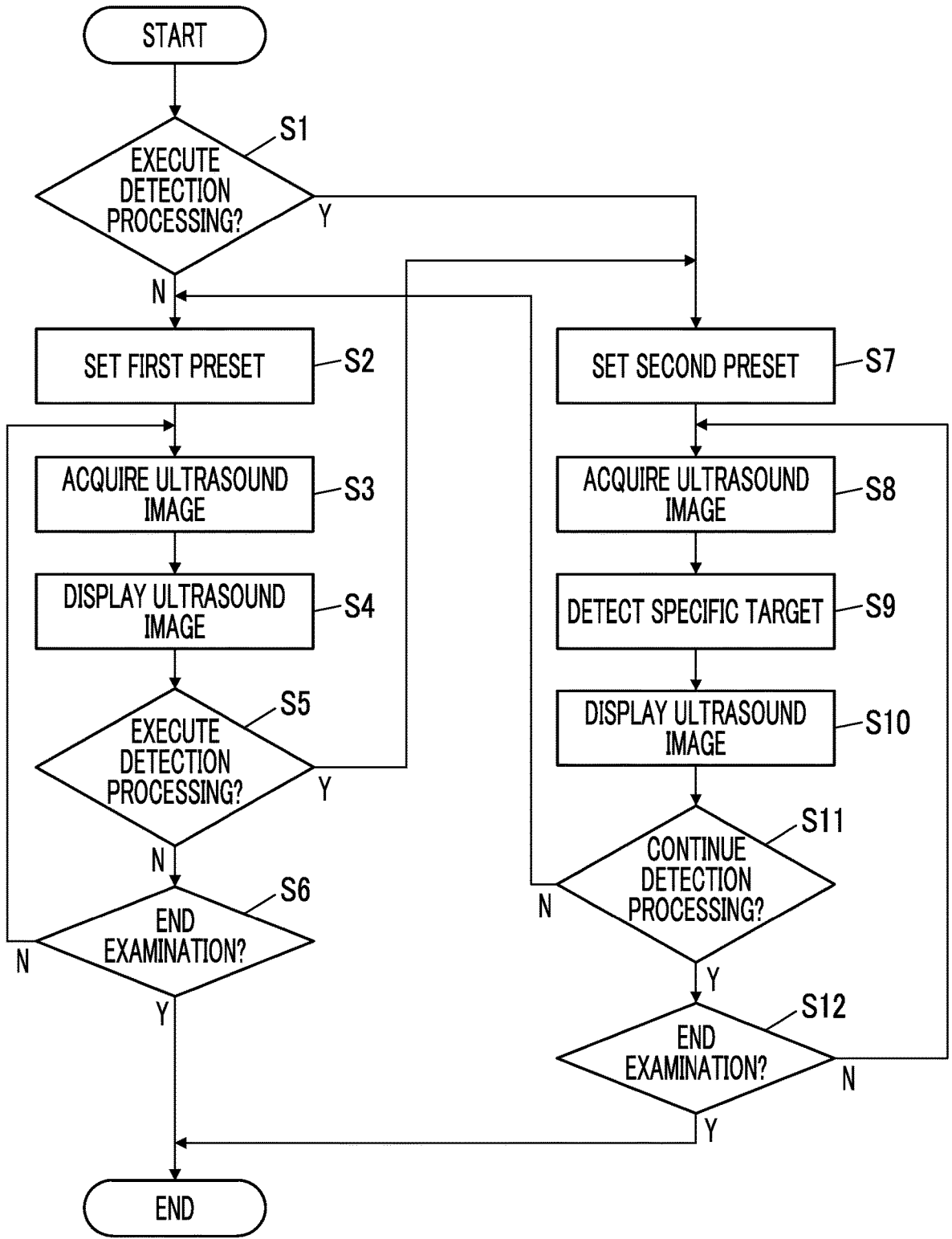
FIG. 6 is a flowchart showing an operation of the ultrasound diagnostic apparatus according to Embodiment of the present invention.

In a case where it is determined in step S6 to end the examination, the operation of the ultrasound diagnostic apparatus according to the flowchart of FIG. 6 is completed.

In a case where it is determined in steps S1 and S5 to execute the detection processing of the specific target T, the process proceeds to step S7. In this case, the specific type of the target T is also designated by the user.

In step S7, the preset setting unit 26 sets the second preset, which is different from the first preset and is used to clearly depict the specific target T designated by the user in step S1 in the ultrasound image U, and supplies the set second preset to the image acquisition unit 31. The second preset is a preset selected according to the specific target T designated by the user.

In step S8, in a state in which the user disposes the ultrasound probe 1 on the body surface of the subject, the image acquisition unit 31 acquires the ultrasound image U using the second preset supplied in step S7. The ultrasound image U acquired here clearly depicts the specific target T designated by the user in step S1.

In step S9, the specific target detection unit 25 uses a machine learning model that has learned in advance a large number of ultrasound images U showing the specific target T to detect the specific target T from the ultrasound image U acquired in step S8. Since the ultrasound image U clearly depicts the specific target T, the specific target detection unit 25 can detect the specific target T with high accuracy.

In step S10, the display controller 22 displays the ultrasound image U acquired in step S8 on the monitor 23. In this case, the display controller 22 can display the target T with emphasis on the monitor 23, for example, as shown in FIG. 5, by emphasizing the contour C of the target T in the ultrasound image U. As a result, the user can easily grasp the presence of the target T. Further, the display controller 22 can display on the monitor 23 the message M2 indicating that the specific target detection unit 25 is in the operation state and the icon A2 indicating that the second preset is set. As a result, the user can easily grasp that the detection processing of the specific target T is operating and the content of the second preset that is currently set.

In step S11, the detection controller 24 determines whether or not to continue the detection processing of the specific target T through the specific target detection unit 25. In this case, the detection controller 24 can determine to continue the detection processing of the specific target T, for example, in a case where no particular instruction to not detect the target T is input from the user via the input device 28. In addition, the detection controller 24 can determine to stop the detection processing of the specific target T, for example, in a case where an instruction to not detect the target T is input from the user via the input device 28.

In a case where it is determined in step S11 to continue the detection processing of the specific target T, the process proceeds to step S12. In step S12, the main body controller 27 determines whether or not to end the examination of the subject that is currently being performed.

In a case where it is determined in step S12 to continue the examination, the process returns to step S8, and the ultrasound image U is newly acquired using the second preset. In subsequent step S9, the processing of detecting the specific target T from the ultrasound image U is performed, the ultrasound image U is displayed on the monitor 23 in step S10, and it is determined in step S11 whether or not to execute the detection processing of the specific target T. In a case where it is determined in step S11 to continue the detection processing of the specific target T, the process proceeds to step S12. In this manner, as long as it is determined in step S11 to continue the detection processing of the target T and it is determined in step S12 to continue the examination, the processing of steps S8 to S12 is repeated.

In a case where it is determined in step S11 to stop the detection processing of the specific target T, the process proceeds to step S2, the first preset is set by the preset setting unit 26, and the set first preset is supplied to the image acquisition unit 31. Since the subsequent processing after step S3 has already been described, the description thereof will be omitted.

In a case where it is determined in step S12 to end the examination, the operation of the ultrasound diagnostic apparatus according to the flowchart of FIG. 6 is completed.

From the above, with the ultrasound diagnostic apparatus of the embodiment, the image acquisition unit 31 acquires the ultrasound image U of the subject using the ultrasound probe 1 and in accordance with the plurality of parameters related to the image acquisition, the specific target detection unit 25 detects the specific target T from the ultrasound image U using the machine learning model, and the preset setting unit 26 sets the different presets during the operation and during the non-operation of the specific target detection unit 25 for the predetermined preset among the plurality of parameters and supplies the set preset to the image acquisition unit 31. Therefore, the ultrasound image U clearly depicting the specific target T is acquired during the operation of the specific target detection unit 25, and the detection accuracy of the target T by the specific target detection unit 25 can be improved.

Although it has been described that the transmission and reception circuit 12 is provided in the ultrasound probe 1, the transmission and reception circuit 12 may be provided in the apparatus main body 2.

In addition, although it has been described that the image generation unit 21 is provided in the apparatus main body 2, the image generation unit 21 may be provided in the ultrasound probe 1.

Further, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

In addition, the preset setting unit 26 can also automatically determine and set the preset corresponding to the target T detected from the ultrasound image U, and supply the set preset to the image acquisition unit 31 during the operation of the specific target detection unit 25. As a result, since the user does not need to manually switch the types of the target T, for example, even in a case where the target T that the user wants to observe is changed during the examination, the examination can proceed smoothly.

EXPLANATION OF REFERENCES

1: ultrasound probe
2: apparatus main body
11: transducer array
12: transmission and reception circuit
21: image generation unit
22: display controller
23: monitor
24: detection controller
25: specific target detection unit
26: preset setting unit
27: main body controller
28: input device
31: image acquisition unit
32: processor
41: pulsar
42: amplification section
43: AD conversion section
44: beam former
45: signal processing section
46: DSC
47: image processing section
A1, A2: icon
C: contour
M1, M2: message
T: target
U: ultrasound image

What is claimed is:

1. An ultrasound diagnostic apparatus comprising:
an ultrasound probe; and
a processor configured to
acquire an ultrasound image of a subject using the ultrasound probe and in accordance with a plurality of parameters related to image acquisition, and
perform a detection processing of a specific target from the ultrasound image using a machine learning model,
wherein the processor is further configured to operate either in a first mode to not perform the detection processing or in a second mode to perform the detection processing, based on an instruction from a user,
wherein the processor is further configured to, for a predetermined preset among the plurality of parameters, set first presets during the first mode, and
acquire a first ultrasound image based on any one of the first presets,
wherein the processor is further configured to receive a first target designated by the user during the second mode,
for a predetermined preset among the plurality of parameters, set second presets that correspond to the first target and differ from the first presets,
acquire a second ultrasound image based on any one of the second presets,
perform the detection processing of the first target from the second ultrasound image acquired based on any one of the second presets using a first machine learning model that has learned in advance a large number of ultrasound images showing the first target inside the subject,
wherein the processor is further configured to perform a detection processing of, as the specific target, any of an organ, a blood vessel, a stool present inside a large intestine, a urine present inside a bladder, a nerve, an ascites fluid, a pleural fluid, a suspected abnormal site, or a B-line from the second ultrasound image using the machine learning model, and wherein the processor is further configured to set at least one preset of a depth, a harmonic, a spatial compound, an acoustic power, a sound velocity, a steer, an ultrasound frequency, a gain, a dynamic range, or a contrast as any one of the second presets.

2. The ultrasound diagnostic apparatus according to claim 1, further comprising:

a monitor configured to display the ultrasound image, wherein the processor is further configured to display the first ultrasound image during the first mode and the second ultrasound image during the second mode on the monitor in different modes.

3. The ultrasound diagnostic apparatus according to claim 2, wherein the processor is further configured to display the first presets during the first mode on the monitor, and display the second presets during the second mode on the monitor.

4. The ultrasound diagnostic apparatus according to claim 1, wherein the machine learning model has learned in advance a large number of ultrasound images showing the specific target inside the subject, and receives an input of the second ultrasound image and automatically analyzes the input second ultrasound image to output a detection result of the specific target.

5. The ultrasound diagnostic apparatus according to claim 2, wherein the machine learning model has learned in advance a large number of ultrasound images showing the specific target inside the subject, and receives an input of the second ultrasound image and automatically analyzes the input second ultrasound image to output a detection result of the specific target.

6. The ultrasound diagnostic apparatus according to claim 3, wherein the machine learning model has learned in advance a large number of ultrasound images showing the specific target inside the subject, and receives an input of the second ultrasound image and automatically analyzes the input second ultrasound image to output a detection result of the specific target.

7. A control method of an ultrasound diagnostic apparatus comprising:

acquiring an ultrasound image of a subject using a ultrasound probe and in accordance with a plurality of parameters related to image acquisition;

performing a detection processing of a specific target from the ultrasound image using a machine learning model, wherein the ultrasound diagnostic apparatus operates either in a first mode to not perform a detection processing or in a second mode to perform the detection processing, based on an instruction from a user, wherein, for a predetermined preset among the plurality of parameters, first presets is set during the first mode, and a first ultrasound image is acquired based on any one of the first presets, wherein, a first target designated by the user is received during the second mode, for a predetermined preset among the plurality of parameters, second presets that correspond to the first target and differ from the first presets is set, a second ultrasound image is acquired based on any one of the second presets, and the detection processing of the first target is performed from the second ultrasound image acquired based on any one of the second presets using a first machine learning model that has learned in advance a large number of ultrasound images showing the first target inside the subject, wherein a detection processing of, as the specific target, any of an organ, a blood vessel, a stool present inside a large intestine, a urine present inside a bladder, a nerve, an ascites fluid, a pleural fluid, a suspected abnormal site, or a B-line is performed from the second ultrasound image using the machine learning model, and wherein at least one preset of a depth, a harmonic, a spatial compound, an acoustic power, a sound velocity, a steer, an ultrasound frequency, a gain, a dynamic range, or a contrast is set as any one of the second presets.

* * * * *